US00PP35944P2

(12) United States Plant Patent
Hansen

(10) Patent No.: US PP35,944 P2
(45) Date of Patent: Jul. 2, 2024

(54) ***HOSTA* PLANT NAMED 'DANCING ON THE SUN'**

(50) Latin Name: ***Hosta* hybrid (Tratt.)**
Varietal Denomination: Dancing on the Sun

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 18/445,630

(22) Filed: Nov. 29, 2023

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

*Primary Examiner* — Susan McCormick Ewoldt

(57) ABSTRACT

A new and distinct *Hosta* plant named 'Dancing on the Sun' produces large rounded mounds of broadly lanceolate to narrowly cordate leaves of yellowish color. The large-sized leaves have a matte upper surface and glaucous underside. The flowers are white with light lavender centers and pale lavender backs. Flowers are attractively subtended by floral bracts making the whole scape more effective. 'Dancing on the Sun' is useful in the landscape, as a container plant, a specimen, or en masse.

2 Drawing Sheets

Botanical classification: *Hosta* hybrid (Tratt.).
Variety denomination: 'Dancing on the Sun'.

STATEMENT REGARDING PRIOR DISCLOSURES UNDER 37 CFR 1.77(B)(6)

*Hosta* 'Dancing on the Sun' was first introduced by the inventor as a non-enabling description in registration of the name in early 2023 with the International Cultivar Registration Authority for the genus *Hosta*. No plants of *Hosta* 'Dancing on the Sun' have been sold or offered for sale in this country or anywhere in the world, nor has any enabling disclosure of the new plant been made.

BACKGROUND AND ORIGIN OF THE PLANT

The present invention relates to a new and distinct *Hosta* plant, *Hosta* 'Dancing on the Sun' hereinafter also referred to as the new plant or by the cultivar name, 'Dancing on the Sun'. *Hosta* 'Dancing on the Sun' was hybridized by the inventor on Aug. 5, 2014, at a wholesale perennial nursery in Zeeland, Michigan, USA. The female parent was the proprietary unreleased hybrid known only by the breeder code 11-253-10 (not patented) and the male parent was a proprietary unreleased hybrid known only by the breeder code 11-304-2 (not patented). The seeds from this cross were planted in late fall of 2014 and a single seedling selection from this cross eventually produced the new plant. The new plant was assigned the breeder code 14-257-1 and passed the initial evaluation in the summer of 2016. 'Dancing on the Sun' has been asexually propagated by division at the same nursery since 2020 and also by careful shoot tip plant tissue culture with the resultant asexually propagated plants having retained all the same traits as the original plant. *Hosta* 'Dancing on the Sun' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Neptune' U.S. Plant Pat. No. 19,674, 'Party Streamers' U.S. Plant Pat. No. 33,277, 'Dancing Queen' (not patented), 'River of Gold' (not patented), 'Seasons in the Sun' U.S. Plant Pat. No. 34,284, and 'Echo the Sun' U.S. Plant patent application Ser. No. 17/300,986.

The female parent (11-253-10) is slightly smaller in habit and in foliage size, and the leaves are not as yellowish color in the summer. The proprietary unnamed male parent (11-304-2) has a larger and less arching habit and the foliage has less undulating margins.

'Neptune' has a slightly smaller habit with bluish-green foliage and longer petioles. 'Party Streamers' is more compact and shorter in habit and has narrower leaf blades and petioles. 'Dancing Queen' has a larger habit with more arching foliage with less sinuate margins, less folding and the yellow spring color becomes chartreuse in the summer. 'River of Gold' has a smaller habit and smaller leaves that are less sinuate, the leaf color is more chartreuse and less yellowish hue, and the scape is more arching. 'Seasons in the Sun' has a slightly smaller habit, smaller foliage that is more rounded, with a less sharply acute apex, and the margin is less sinuate. 'Echo the Sun' has a smaller habit and foliage, the leaves are more folded, and the scape is more erect and less arching.

Other *Hosta* cultivars may have individual traits similar to 'Dancing on the Sun' but the new plant differs from the above-listed cultivars and all other *Hostas* known to the applicant, by the combination of the following traits.

1. Leaves are large-sized, broadly lanceolate to narrowly cordate, with narrowly acute apices and cordate bases;
2. Leaves are predominately flat with nicely rippled margins;

3. Leaves are yellowish with the top surface matte and the bottom surface glaucous;
4. Flower tepals are white with light lavender centers and pale lavender backs;
5. Flowers are densely arranged on scapes with the first flowers beginning to open above the foliage;
6. Floral bracts of light yellowish-green with a blush of lavender subtend each flower;
7. The habit is a large-sized rounded mound.

BRIEF DESCRIPTION OF THE DRAWING

The photograph of the new plant demonstrates the overall appearance of the new plant, including the unique traits. The colors are as accurate as reasonably possible with color reproductions. Ambient light spectrum, temperature, source, and direction may cause the appearance of minor variations in color.

The drawings show an eight-year-old 'Dancing on the Sun' plant in a trial garden at a nursery in Zeeland, MI with supplement fertilizer and water as needed.

DETAILED BOTANICAL DESCRIPTION

Figure 1:
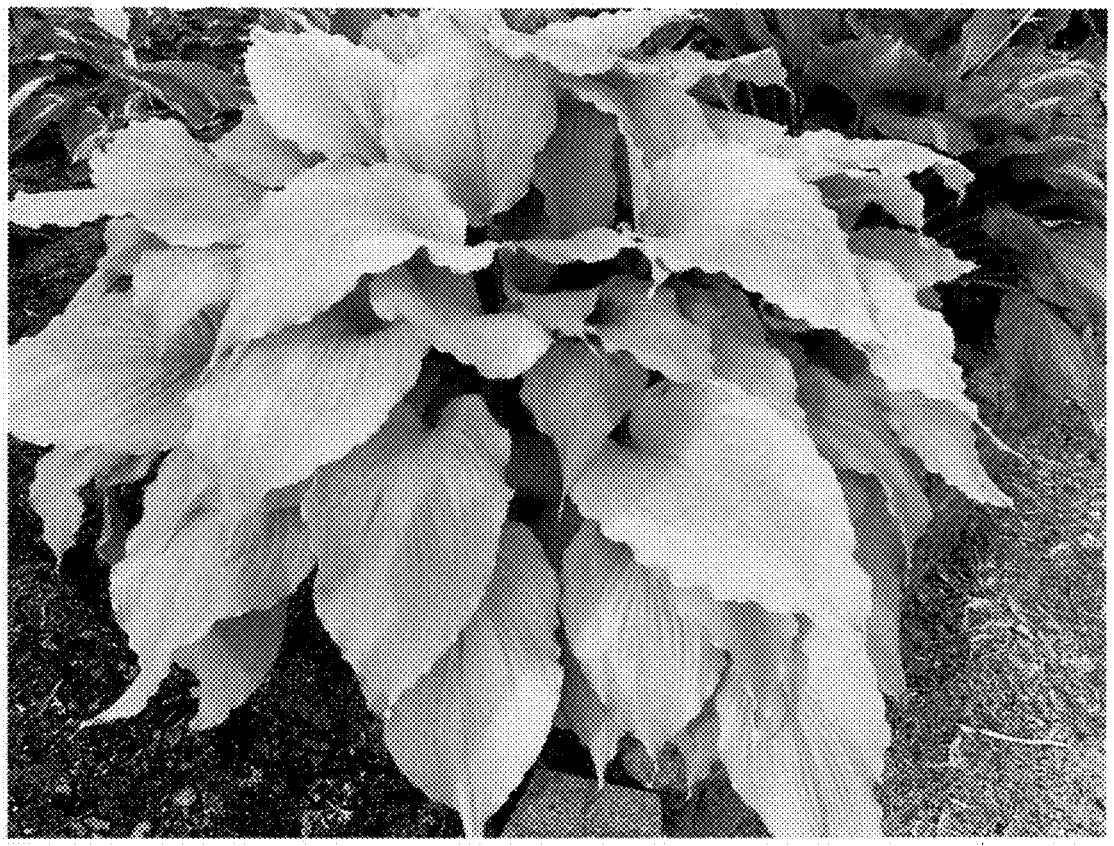
FIG. 1 shows the landscape foliage habit of a new plant prior to flowering.
Figure 2:
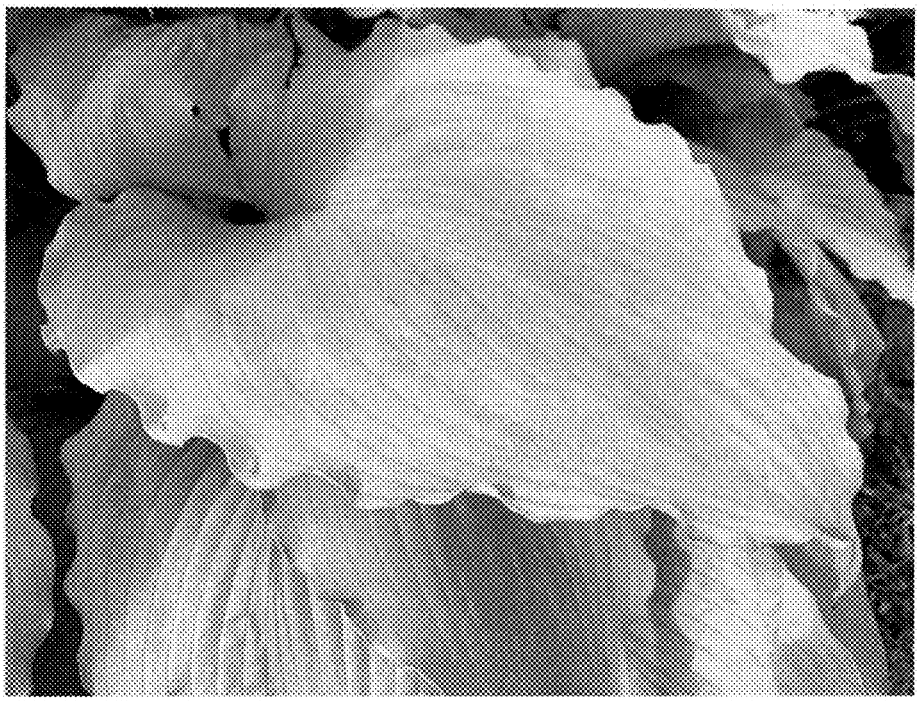
FIG. 2 shows a close-up of a leaf.
Figure 3:
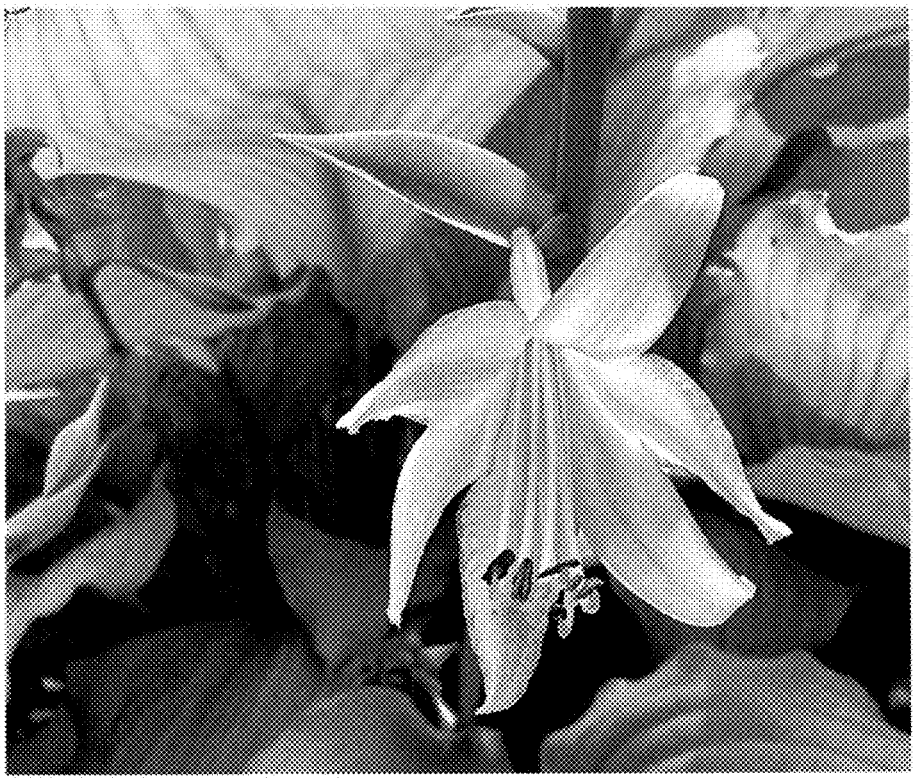
FIG. 3 shows a close-up of the flower, buds, and flower foliar bracts.

The following descriptions and color references are based on the 2015 edition of The Royal Horticultural Society Colour Chart except where common dictionary terms are used. The new plant, *Hosta* 'Dancing on the Sun', has not been observed under all possible environments. Those skilled in the art will appreciate that certain characteristics will vary with plants that are more mature or plants that are less mature. The phenotype may vary slightly with different environmental conditions, such as temperature, light, fertility, moisture, and maturity levels, but without any change in the genotype. The following observations and size descriptions are of an eight-year-old plant in a shaded trial garden in Zeeland, Michigan with supplemental water and fertilizer.

Botanical classification: *Hosta* x hybrid;

Parentage: Female or seed parent is 11-253-10; male or pollen parent is 11-304-2;

Propagation: Garden division and sterile shoot tip tissue culture;

Time to initiate roots from tissue culture: About two to three weeks;

Growth rate: Moderately vigorous;

Crop time: About three months to four months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with a basal rosette of leaves emerging from rhizomes producing a large-sized arching upright mound of outwardly extending petioles and leaves and arching scapes flowering above the foliage;

Plant size: Foliage height to about 78 cm above the soil line to the top of the leaves, to about 117 cm tall to the top of the flowers, and to about 165 cm wide at the widest point just above the soil line;

Foliage description: Broadly lanceolate to narrowly cordate; narrowly acute apex, cordate base; margin entire and strongly sinuate; predominately flat; glabrous both surfaces, smooth, and adaxial matte and abaxial glaucous; flexible but stiff;

Leaf blade size: To about 40.6 cm long and about 24.1 cm wide about one-third way from the base; average about 36.5 cm long and 22 cm wide; not variegated;

Leaf blade color: Early season and expanding adaxial between RHS 146D and RHS 145A, abaxial between RHS 145A and RHS 146D; mid-season and mature adaxial variable, between RHS 145A and RHS 146D in heavy shade, and higher light between RHS 160B and RHS 162B, and between RHS 162D and RHS 158A, abaxial variable, between RHS 148D and RHS 146D, and between RHS 160A and RHS 160B;

Veins: 13 to 15 pairs plus midrib; slightly impressed adaxial and costate and smooth abaxial;

Vein color: Young adaxial nearest RHS 145C, abaxial between RHS 145A and RHS 146D; mature adaxial variable, nearest RHS 146D; mature abaxial between RHS N144D and RHS 145A;

Petiole: Glabrous and moderately glaucous both adaxial and abaxial; moderately concavo-convex; stiff; to 49 cm long and 18 mm wide at base and about 9 mm deep, average about 42 cm long and 15 mm wide and 6 mm deep;

Petiole color: Adaxial and abaxial between RHS 145C and RHS 146D;

Flower description:

Buds one to two days prior to opening: Clavate with acute apex and narrow tube and rounded base; about 52 mm long and 15 mm in diameter at the widest portion in the bulb, tube to about 20 mm long and to about 3.0 mm diameter;

Bud color: Distally nearest RHS 85B transitioning to the basal 10 mm nearest RHS 157D;

Flowers: Perfect; incomplete; irregularly flared campanulate; attitude outwardly to slightly drooping; to 76 mm long to exserted pistil; corolla to 74 mm long and 45 mm wide at apex, fused in basal 44 mm, free in the distal 30 mm; corolla tube portion 25 mm long and 3 mm diameter; decreasing in size distally; with rounded base; flowers tightly arranged on scape;

Flowering lasting: Persists for a normal period, usually about one day on plant;

Flowering period: Scapes remain effective with flowers beginning late July for about three and a half weeks; with about 45 flowers per scape; mostly secund;

Fragrance: No detectable fragrance;

Tepal: Two sets of three; lanceolate; entire margins; acute apex; fused in basal 44 mm, free in distal 30 mm; glabrous adaxial and abaxial; outer set to about 10 mm wide and 74 mm long; inner set to about 12 mm wide and 74 mm long;

Tepal color: Inner and outer set adaxial 3 mm longitudinal center nearest RHS 85C and along edges nearest RHS NN155D along edges, inner set with a 0.5 mm transparent margin; inner and outer set abaxial with a faint blush of nearest RHS 85D along center and nearest RHS NN155D along margin with a transparent 0.5 margin on the inner set;

Gynoecium: Single; to about 76 mm long; superior;

*Style*.—Cylindrical; glabrous; to about 69 mm long and 0.7 mm diameter; proximally straight with distal 8 mm arcuate upwards 90°; color nearest RHS 145D proximally and nearest RHS 155D distally.

*Stigma*.—Puberulent; globose; about 1 mm long and 1 mm diameter; color nearest RHS 155B.

*Ovary*.—Ellipsoidal; superior; apex rounded; base rounded to truncate; sides lightly furrowed, about 6 mm long and 2.5 mm diameter; color nearest RHS 145A.

Androecium: Six;

*Filaments*.—Six; cylindrical; approximately 64 mm long and 0.5 mm in diameter; arcuate upwardly about 90° in the distal 6 mm; color in distal one-half nearest RHS 155D transitioning to nearest RHS 145D in the proximal one-third.

*Anthers*.—Ellipsoidal with rounded apices; basifixed, longitudinally dehiscent; about 5 mm long and 2 mm wide when fully developed; color nearest RHS 199B.

*Pollen*.—Abundant; spherical; less than 0.1 mm long; color nearest RHS 17B.

Peduncle: Cylindrical; usually one per mature division; about 15 per plant; glabrous; moderately glaucous; slightly arching; to about 117 cm long, and about 8 mm in diameter at the base, average about 96 cm tall and 7 mm diameter at base;

Inflorescence: Flowering portion about 32 cm long and 9 cm wide; with bracts subtending each flower;

Peduncle color: Proximal portion below leaves between RHS 146D and RHS 145A, distal portion nearest RHS 146D;

Pedicel: Cylindrical; glabrous; slightly lustrous; to about 25 mm long and 1.7 mm diameter, decreasing distally; attitude arcuate outwardly to slightly downward;

Pedicel color: Nearest RHS 146D;

Floral bracts: Each flower normally subtended by a single lanceolate bract; narrowly acute apex and truncate base; entire margin; glabrous and slightly glaucous abaxial and adaxial; to about 30 mm long 10 mm wide, decreasing distally;

Bract color: At flowering adaxial and abaxial between RHS 146D and RHS N144A, with young buds margins nearest RHS 148D with variable blush of nearest RHS 85D;

Fruit: Non-fleshy, dehiscent, tri-loculicidal capsule; oblong ellipsoidal; rounded base; apiculate apex; about 31 mm long and 7 mm in diameter; color as maturing nearest RHS 146D, when nearly mature and prior to dehiscence nearest RHS 146C distally and between RHS 146D and RHS 145A proximally, and upon dehiscence nearest RHS 161C;

Seeds: Elliptic; with flattened wing surrounding embryo positioned toward one end of the ellipse; about 9 mm long, 3 mm wide, and 1 mm thick at embryo; typically 24 to 36 per capsule; color nearest RHS 200A with maturity;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The plant grows best and shows the best coloration with plenty of moisture, adequate drainage, and light shade, but is able to tolerate some drought when mature.

Hardiness: At least from USDA zone 3 through 8, and other disease resistance is typical of that of other *Hostas*.

It is claimed:

1. A new and distinct *Hosta* plant named *Hosta* 'Dancing on the Sun' as herein described and illustrated.

* * * * *